US008026281B2

(12) United States Patent
Doyle, Jr. et al.

(10) Patent No.: US 8,026,281 B2
(45) Date of Patent: Sep. 27, 2011

(54) TREATING METABOLIC SYNDROME WITH FENOFIBRATE

(75) Inventors: Ralph T. Doyle, Jr., Milford, NJ (US); Douglas F. Kling, Parisippany, NJ (US); Roelof M. L. Rongen, Caliton, NJ (US); Keith S. Rotenberg, Danville, NJ (US)

(73) Assignee: Lupin Atlantis Holdings, S.A., Schaffhausen (CH)

( * ) Notice: Subject to any disclaimer, the term of this patent is extended or adjusted under 35 U.S.C. 154(b) by 0 days.

(21) Appl. No.: 11/111,971

(22) Filed: Apr. 22, 2005

(65) Prior Publication Data

US 2006/0083783 A1    Apr. 20, 2006

Related U.S. Application Data

(60) Provisional application No. 60/618,181, filed on Oct. 14, 2004.

(51) Int. Cl.
A61K 31/19 (2006.01)
A61K 9/48 (2006.01)
A61K 9/20 (2006.01)

(52) U.S. Cl. .................. 514/571; 424/452; 424/465

(58) Field of Classification Search .......... 514/310, 514/557, 571; 424/456, 452, 458, 465
See application file for complete search history.

(56) References Cited

U.S. PATENT DOCUMENTS

| 3,907,792 | A * | 9/1975 | Mieville ............ 544/162 |
| 4,895,726 | A | 1/1990 | Curtet et al. |
| 5,545,628 | A | 8/1996 | Deboeck et al. |
| 5,645,856 | A | 7/1997 | Lacy et al. |
| 5,827,536 | A | 10/1998 | Laruelle |
| 6,074,670 | A | 6/2000 | Stamm et al. |
| 6,096,338 | A | 8/2000 | Lacy et al. |
| 6,267,985 | B1 | 7/2001 | Chen et al. |
| 6,667,064 | B2 | 12/2003 | Surette |
| 6,720,001 | B2 | 4/2004 | Chen et al. |
| 7,101,574 | B1 | 9/2006 | Criere et al. |
| 7,863,331 | B2 | 1/2011 | Criere et al. |
| 2003/0082215 | A1 | 5/2003 | Lemut et al. |
| 2003/0194442 | A1 | 10/2003 | Guivarch et al. |
| 2003/0235595 | A1* | 12/2003 | Chen et al. ............ 424/400 |
| 2004/0052824 | A1 | 3/2004 | Abour Chacra-Vernet et al. |

FOREIGN PATENT DOCUMENTS

| EP | 0 330 532 B1 | 8/1989 |
| WO | WO 99/29300 A1 | 6/1999 |
| WO | WO 01/21154 A2 | 3/2001 |

OTHER PUBLICATIONS

Vega et al., "Free fatty acid metabolism during fenofibrate treatment of the metabolic syndrome", CLinical Pharmacology & Therapeutics, vol. 74, pp. 236-244 (2003).*
Vega et al., "Effects of Adding Fenofibrate (200 mg/day) to Simvastatin (10 mg/day) in Patients With Combined Hyperlipidemia and Metabolic Syndrome", American Journal of Cardiology, vol. 91, pp. 956-960 (2003).*
Wysocki et al., "Effects of micronized fenofibrate on insulin resistance in patients with metabolic syndrome", International Journal of Clinical Pharmacology and Therapeutics, vol. 42, No. 4, pp. 212-217 (Apr. 2004).*
Definittion of Miconized by the Free Online Dictionary and Definition of micro- and granule from Dictionary.com (2006).*
Ballantyne, C.M, et al., "*Efficacy of Resuvastatin 10 mg in Patients with the Metabolic Syndrome*", AmJCardiology, 91(5A); 2003, pp. 25C-27C.
Tenenbaum, A., et al., "*Peroxisome Proliferator—Activated Receptor Ligand Bezafibrate for Prevention of Type 2 Diabetes Mellitus in Patients with Coronary Artery Disease*", Circulation; 2004; pp. 2197-2202.
Grundy, S.M., "*Metabolic Syndrome: A Growing Clinical Challenge*", Medscape Cardiology 8(2), 2004, 12 pp.
Garber, A.J., "*Attenuating Cardiovascular Risk Factors in Patients with Type 2 Diabetes*", American Family Physician, 2000; 13 pp.
Nagai, Y. et al., "*Amelioration of high fructose-induced metabolic derangements by activation of PPARα*", AmJPhysiolEndocrinolMetab., 282, 2002, pp. E1181-1190.
Watts, G., et al., "*Differential Regulation of Lipoprotein Kinetics by Atorvastatin and fenofibrate in Subjects with the Metabolic Syndrome*", Diabetes, 42, 2003, pp. 803-811.
Capell, W.H., et al., "*Short-Term Triglyceride Lowering With Fenofibrate Improves Vasodilator Function in Subjects with Hypertriglyceridemia,*" Arterioscler Thromb Vasc Biol., 2003, pp. 307-313.
Cortellaro, M., et al., "*Effects of Fluvastatin and Bezafibrate Combination on Plasma Fibrinogen, t-plasminogen plasminogen Activator Inhibitor and C Reactive Protein levels in Coronary Artery Disease Patients with Mixed Hyperlipidaemia (FACT Study)*", Thromb Haemost, 2000, pp. 549-553.
Staels, M., et al., "*Mechanism of Action of Fibrates on Lipid and Lipoprotein Metabolism*", Circulation (Cardiovascular Drugs), 1998, pp. 2088-2093.
Davidson et al., Clin. Ther., "Efficacy and Safety Profile of Fenofibrate-Coated Microgranules 130 mg, With and Without Food, in Patients with Hypertriglyceridemia and the Metabolic Syndrome: An 8-Week, Randomized, Double-Blind, Placebo-Controlled Study," 27(6): 715-727 (2005).
Huth et al., Fortschritte der Therapie, "Dyslipoproteinämie un Diabetes mellitus beim metabolischen Syndrom," 110(11): 72-78 (1992).
Wierzbicki et al., Am. J. Cardiovasc. Drugs, "Drug Treatment of Combined Hyperlipidemia," 1(5): 327-336 (2001).
Fenofibrate Clinical trials retrieved from http://ClinicalTrials.gov; 10 pages "last updated date Jan. 7, 2011".

* cited by examiner

Primary Examiner — Kevin E Weddington
(74) Attorney, Agent, or Firm — Leydig, Voit & Mayer, Ltd.

(57) ABSTRACT

A method of treating metabolic syndrome in a human diagnosed with metabolic syndrome by administering a therapeutically effective amount of fenofibrate over a treatment period. The results can include identifying a human as not having clinical metabolic syndrome after treatment, as compared to having metabolic syndrome before treatment.

40 Claims, No Drawings

TREATING METABOLIC SYNDROME WITH FENOFIBRATE

This application claims the benefit of U.S. Provisional Patent Application Ser. No. 60/618,181 of Ralph Doyle, Douglas Kling, Roelof Rongen, and Keith Rotenberg, titled "System and Method Treating Metabolic Syndrome with Fenofibrate" filed Oct. 14, 2004. The entirety of the provisional patent application is incorporated herein by reference.

FIELD OF THE INVENTION

The present invention relates to a system and method of treating metabolic syndrome with a pharmaceutically effective amount of fenofibrate.

BACKGROUND OF THE INVENTION

Metabolic syndrome (also known as "syndrome X," "dysmetabolic syndrome," "obesity syndrome," "Reaven's syndrome" and interchangeably referred to herein as the "syndrome") has emerged as a growing problem. For example, metabolic syndrome has become increasingly common in the United States. It is estimated that about 47 million adults in the United States have the syndrome.

Metabolic syndrome is generally a constellation of metabolic disorders that all result from, or are associated with, a primary disorder of insulin resistance. Accordingly, the syndrome is sometimes referred to as "insulin resistance syndrome." Insulin resistance is characterized by disorders in which the body cannot use insulin efficiently and the body's tissues do not respond normally to insulin. As a result, insulin levels become elevated in the body's attempt to overcome the resistance to insulin. The elevated insulin levels lead, directly or indirectly, to the other metabolic abnormalities.

Some people are genetically predisposed to insulin resistance, while other people acquire factors that lead to insulin resistance. Acquired factors, such as excess body fat and physical inactivity, can elicit insulin resistance, and more broadly, clinical metabolic syndrome. Because of this relationship between insulin resistance and metabolic syndrome, it is believed that the underlying causes of this syndrome are obesity, physical inactivity and genetic factors. In fact, most people with insulin resistance and metabolic syndrome have central obesity (excessive fat tissue in and around the abdomen). The biologic mechanisms at the molecular level between insulin resistance and metabolic risk factors are not yet fully understood and appear to be complex.

Metabolic syndrome is typically characterized by a group of metabolic risk factors that include 1) central obesity; 2) atherogenic dyslipidemia (blood fat disorders comprising mainly high triglycerides ("TG") and low HDL-cholesterol (interchangeably referred to herein as "HDL") that foster plaque buildups in artery walls); 3) raised blood pressure; 4) insulin resistance or glucose intolerance (the body can't properly use insulin or blood sugar); 5) prothrombotic state (e.g., high fibrinogen or plasminogen activator inhibitor in the blood); and 6) a proinflammatory state (e.g., elevated high-sensitivity C-reactive protein in the blood). The National Cholesterol Education Program (NCEP) Adult Treatment Panel (ATP) III guidelines define metabolic syndrome by the following five clinical parameters: a) a waist circumference greater than 102 cm for men, and greater than 88 cm for women; b) a triglyceride level greater than 150 mg/dl; c) an HDL-cholesterol less than 40 mg/dl for men, and less than 50 mg/dl for women; d) a blood pressure greater than or equal to 130/85 mmHG; and e) a fasting glucose greater than 110 mg/dl.

According to the American Heart Association, however, there are no well-accepted criteria for diagnosing the metabolic syndrome. Some guidelines suggest that metabolic syndrome involves four general factors: obesity; diabetes; hypertension; and high lipids. According to the NCEP ATP III guidelines above, the presence of at least three of these five factors meets the medical diagnosis of metabolic syndrome.

Although there is no complete agreement on the individual risk or prevalence of each factor, it is known that the syndrome, as generally agreed upon by those skilled in the field, poses a significant health risk to individuals. A person having one factor associated with the syndrome has an increased risk for having one or more of the others. The more factors that are present, the greater the risks to the person's health. When the factors are present as a group, i.e., metabolic syndrome, the risk for cardiovascular disease and premature death is very high.

For example, a person with the metabolic syndrome is at an increased risk of coronary heart disease, other diseases related to plaque buildups in artery walls (e.g., stroke and peripheral vascular disease), and type 2 diabetes. It is also known that when diabetes occurs, the high risk of cardiovascular complications increases.

Generally, patients suffering from the syndrome are prescribed a change in lifestyle, i.e., an increase in exercise and a change to a healthy diet. The goal of exercise and diet programs is to reduce body weight to within 20% of the "ideal" body weight calculated for age and height.

In some cases, diet and exercise regimens are supplemented with treatments for lipid abnormalities, clotting disorders, and hypertension. For example, patients with the syndrome typically have several disorders of coagulation that make it easier to form blood clots within blood vessels. These blood clots are often a precipitating factor in developing heart attacks. Patients with the syndrome are often placed on daily aspirin therapy to specifically help prevent such clotting events. Furthermore, high blood pressure is present in more than half the people with the syndrome, and in the setting of insulin resistance, high blood pressure is especially important as a risk factor. Some studies have suggested that successfully treating hypertension in patients with diabetes can reduce the risk of death and heart disease by a substantial amount. Additionally, patients have been treated to specifically reduce LDL-cholesterol (interchangeably referred to herein as "LDL") levels, reduce triglyceride levels, and raise HDL levels. Drug treatment of metabolic syndrome as a whole usually includes treatment with a statin or a combination of a statin with either niacin or a fibrate in order to focus on the factors individually.

Specific treatment of high triglyceride levels with lipid-lowering drugs is intended to inhibit cholesterol synthesis in the liver. Fenofibrate or 2-[4-(4-chlorobenzoyl)phenoxy]-2-methyl-propanoic acid, 1-methylethyl ester, which belongs to the fibrate family, has been known for many years as a medicinal active principle because of its efficacy in lowering blood triglyceride and cholesterol levels. Fibrates, such as fenofibrates, supplement the use of lipid-lowering drugs by enhancing catabolism of triglyceride-rich particles and reduce VLDL output. Fibrates also raise HDL and lower triglycerides by activating PPAR-alpha, with upregulated expression of Apo A genes and reduced expression of genes for Apo C-III, PAI-1, and fibrinogen. Fibrates also increase expression of the gene for lipoprotein lipase.

Fibrates are typically orally administered to such patients. A treatment of 30 to 300 mg of fenofibrate per day enables a 20 to 25% reduction of cholesterolemia and a 40 to 50% reduction of triglyceridemia to be obtained.

It is also known that, to obtain a satisfactory hypocholesterolemic effect, it is desirable to maintain a circulating level of fenofibric acid (the active metabolite of fenofibrate). The half-life for elimination of fenofibric acid from the plasma is on the order of 20 hours. Its maximum concentration in the plasma is attained, on average, five hours after ingestion of the medicinal product. The mean concentration in the plasma is on the order of 15 μg/ml for a dose of 300 mg per day. This level is generally stable throughout treatment.

Historically, fenofibrate was available in a pharmaceutical dosage form (Lipidil®) consisting of a hard gelatin capsule containing fenofibrate and pharmaceutically acceptable excipients such as lactose, pregelatinized starch and magnesium stearate. Fenofibrate is also available in another pharmaceutical dosage as Lipidil Micro®. European Patent Application 330,532 and U.S. Pat. No. 4,895,726, both of which are incorporated herein in their entireties, disclose a fenofibrate composition in which the fenofibrate powder is co-micronized with a solid wetting agent or solid surfactant, such as sodium lauryl sulfate. The dosage form exhibits improved dissolution rate and bioavailability of fenofibrate over that of micronized fenofibrate alone or that of micronized fenofibrate subsequently mixed with solid surfactant.

There are no studies that show the use of fibrates only to treat metabolic syndrome as a whole, however. The use of fibrates is only known to treat specific disorders, such as triglyceride levels, and not metabolic syndrome as a whole.

In a study by Ballantyne, C. M., et al, *Efficacy of rosuvostatin 10 mg in patients with metabolic syndrome*, Am. J. Cardiol (2003), 91:25C-27C, a series of clinical trials showed that fibrate therapy reduces the risk of cardiovascular heart disease. In particular, researchers showed that gemfibrozil reduced the risk for major cardiovascular events in high-risk patients, particularly in those with diabetes and insulin resistance. However, this study only examined the use of gemfibrozil on specific disorders, some of which can be part of metabolic syndrome, and not on metabolic syndrome as a whole.

In a study by Tenebaum, A., et al, *Peroxisome proliferators-activated receptor ligand bezafibrate for prevention of type 2 diabetes mellitus in patients with coronary heart disease*, Circulation (2004), 109:2197-2202, bezafibrate was shown to significantly lower all-cause and cardiac mortality in patients with triglyceride levels greater than or equal to 200 mg/dl. Bezafibrate treatment also delayed the onset of type 2 diabetes, increased HDL-cholesterol by 16%, and lowered triglycerides by 24%. Tenebaum et al observed the potential for an increase in LDL-cholesterol with fibrate therapy. The Tenebaum study, however, only measures two of the five NCEP ATP III parameters commonly associated with clinical metabolic syndrome, and thus Tenebaum did not, in fact, measure the effect of fibrate on metabolic syndrome. It has been unknown, therefore, whether fibrate is effective in the treatment of the clinical condition of metabolic syndrome, which includes more than the two parameters examined by Tenebaum.

There is an unmet need in the art for a pharmaceutically effective amount of fenofibrate to treat patients having clinically diagnosed metabolic syndrome. Additionally, there is an unmet need in the art to treat patients with fenofibrate for metabolic syndrome as a whole and not just particular elements that can be part of metabolic syndrome.

SUMMARY OF THE INVENTION

The present invention overcomes the above-mentioned problems, as well as others, by providing a pharmaceutically effective amount of fenofibrate to treat metabolic syndrome as a whole. It is an object of this invention to provide a method of treatment of a human having with metabolic syndrome, the method comprising administration of fenofibrate, preferably as the sole active ingredient in the treatment, to a human diagnosed with metabolic syndrome. Treatment with fenofibrate has been shown to successfully reduce the number of patients having metabolic syndrome in a population of patients with metabolic syndrome.

A second embodiment of the present invention is a novel method for the treatment of metabolic syndrome comprising the administration of fenofibrate once per day in a formulation preferably containing from about 20 to about 400 mg, more preferably from about 30 to about 300 mg, most preferably from about 40 to about 140 mg fenofibrate. In some variations, the administration is repeated once a day for at least 2 weeks, preferably for at least 4 weeks, and more preferably for at least 8 weeks.

In some embodiments, the present invention is directed to reducing triglyceride levels, reducing total cholesterol, reducing mean VLDL-cholesterol, and decreasing lipoproteins in humans having metabolic syndrome.

In some embodiments, the present invention is directed to a method for treating metabolic syndrome in a human. The method first administering a therapeutically effective amount of fenofibrate for a treatment period once daily to a human diagnosed as having metabolic syndrome. The method then comprises determining after the treatment period that the human no longer has metabolic syndrome.

In other embodiments, the present invention is directed to a method for treating metabolic syndrome in a human comprising orally administering 40 to 140 mg of fenofibrate to a human having metabolic syndrome.

The methods of the invention preferably result in achieving at least three of the following (preferably four, most preferably all five): lowering triglyceride levels, raising HDL-cholesterol levels, lowering LDL-cholesterol levels, lowering Apo C-III levels, and/or lowering fibrinogen levels in the human during a treatment period from a baseline level prior to the treatment period.

Other features of the present invention will become apparent. Additional advantages and novel features of the invention will also become more apparent to those skilled in the art upon examination of the following or upon learning by practice of the invention.

DESCRIPTION OF THE PREFERRED EMBODIMENTS

This invention utilizes fenofibrate to treat metabolic syndrome, and not just specific disorders that can be associated with the syndrome. Accordingly, some embodiments of the present invention treat metabolic syndrome. Treatment with fenofibrate, in accordance with the present invention, has been observed to change a patient's diagnosis during the treatment period as having metabolic syndrome prior to treatment to not having metabolic syndrome after the treatment. Preferably, fenofibrate is the sole active ingredient in the treatment.

Other embodiments of the present invention are directed to novel methods for the treatment of metabolic syndrome comprising the administration of fenofibrate once per day in a formulation preferably containing from about 20 to about 400 mg, more preferably from about 30 to about 300 mg, most preferably from about 40 to about 140 mg fenofibrate.

The treatment period for treating metabolic syndrome can be at least 2 weeks. Preferably the treatment period is at least 4 weeks, and more preferably, the treatment period is at least 8 weeks.

In some embodiments of the present invention, fenofibrate is orally ingested by the patient once per day. There is no specific time of day required; however, it is preferred that the patient take fenofibrate consistently at relatively the same time of day.

Formulations for fenofibrate are generally known to those skilled in the art. European Patent Application 330,532 and U.S. Pat. No. 4,895,726 are incorporated herein in their entireties. Typically, fenofibrate is delivered orally in the form of microgranules (also interchangeably known as "granules") contained in a tablet, capsule, or any other form of oral delivery that is currently known or will be known in the art. One variation of the invention provides an immediate-release fenofibrate composition.

The active ingredients of the present invention fenofibrate may be administered with a combination of one or more non-active pharmaceutical ingredients (also known generally herein as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. Thus, the non-active ingredients may include colloidal silicon dioxide, crospovidone, lactose monohydrate, lecithin, microcrystalline cellulose, polyvinyl alcohol, povidone, sodium lauryl sulfate, sodium stearyl fumarate, talc, titanium dioxide and xanthum gum.

It is known to those skilled in the art that fenofibrate has been conventionally found to have a limited bioavailability through oral ingestion. To improve intestinal absorption fenofibrate has been micronized with a wetting agent or surfactant known in the art. There have been a number of improvements in dosage forms of fenofibrate in an effort to increase bioavailability of the drug and hence its efficacy. U.S. Pat. No. 6,074,670, U.S. Pat. No. 5,827,536, U.S. Pat. Nos. 5,645,856 and 6,096,338, U.S. Pat. No. 6,096,338, U.S. Pat. No. 6,267,985, U.S. Pat. No. 6,667,064, U.S. Pat. No. 6,720,001, U.S. Pat. No. 5,545,628, U.S. Patent Application Publication No. 2003/0082215, U.S. Patent Application Publication No. 2004/0052824, WO 99/29300 and WO 2001/021154 are incorporated herein in their entireties. Fenofibrate, in conjunction with a wetting agent or surfactant that is known or will be known in the art, is known to increase bioavailability of fenofibrate.

In a general pharmaceutical formulation of fenofibrate, fenofibrate is provided in granules sufficient to include a pharmaceutically effective amount of fenofibrate. The granules comprise a neutral core, an active layer (i.e., fenofibrate) surrounding the core, and an outer layer, such as a hydrosoluble binder encompasses the neutral core and the active layer.

A practical formulation of pharmaceutically effective fenofibrate includes fenofibrate combined with an inert hydrosoluble carrier and a surfactant. The hydrosoluble carrier is generally hydrophilic, pharmaceutically inert, crystalline or amorphous. The carrier is soluble in an aqueous medium, preferably gastric acid. Any suitable (e.g., amphoteric, non-ionic, cationic or anionic) surfactant can be used. Examples of surfactants include sodium lauryl sulfate, monooleate, monolaureate, monopalmitate, and monostearate. Excipients, such as sugars or sugar derivatives (e.g., lactose, saccharose, hydrolyzed starch) may also be added.

Specific compositions and formulations of fenofibrate are generally known in the art, particularly in the issued patents and patent applications listed above. An exemplary formulation of fenofibrate presented in a soft capsule. In this formulation, fenofibrate is micronized to obtain a powder, wherein the particles are smaller than 10 µm, and is mixed with diethylene glycol monoethyl ether (DGME) until dissolution of the fenofibrate. The solution is then packaged in capsule form.

In some embodiments of the present invention, triglyceride levels are lowered by administering fenofibrate for a treatment period and frequency as described above in humans diagnosed with metabolic syndrome. In one variation, the triglyceride level during the treatment period compared to a baseline prior to the treatment period is lowered by at least 25%, preferably by at least 30%, and more preferably by at least 35%. In another variation, the triglyceride level during the treatment period, as compared to a baseline prior to the treatment period, is lowered by at least 100 mg/dl, preferably 125 mg/dl, and more preferably by at least 150 mg/dl.

Additionally, in other variations of the present invention, administering fenofibrate has lowered LDL-cholesterol levels, raised HDL-cholesterol levels, lowered Apo C-III levels, and/or lowered fibrinogen levels during the treatment period compared to a baseline prior to the treatment period.

Moreover, in some variations, administering fenofibrate to the human diagnosed with metabolic syndrome at a baseline level before a treatment period results in determining that the human is no longer determined to have or be diagnosed with metabolic syndrome after the treatment period.

A clinical trial report further demonstrating the effectiveness of the present invention is described hereafter.

A Randomized Double-Blind, Double-Dummy, Placebo-Controlled, Phase III Study To Assess The Efficacy And Safety Of 130 MG Of Fenofibrate, With And Without Food, Versus A Matching Placebo, Combined With A Low Saturated-Fat Diet In Subjects With Hypertriglyceridemia And Metabolic Syndrome.

Objectives: A primary outcome variable was the difference in the prevalence of metabolic syndrome between the group treated with 130 mg of fenofibrate ("the treatment group") versus the placebo group ("the placebo"). A related outcome variable included the effect of food on fenofibrate efficacy.

Methodology: This was a multicenter, prospective, double-blind, double-dummy, randomized, placebo-controlled, parallel group study of a micronized formulation of fenofibrate at a single daily dose of 130 mg. Subjects took prescription or over-the-counter lipid lowering medications or dietary supplements known to alter lipid levels or other aspects of the lipid profile until week 6 (visit 1). At week 6, subjects were instructed to follow the therapeutic lifestyle changes diet, in accordance with the Food and Drug Administration guidelines for clinical evaluations of lipid-altering agents.

Also at week 6, qualifying subjects were stratified by triglyceride level and randomized in a double-blind fashion to one of three groups, the first two of which constituted the treatment group and the third group constituted the placebo: A) 1 fenofibrate capsule (130 mg) with food and 1 placebo capsule without food; B) 1 fenofibrate capsule (130 mg) without food (three hours after a meal) and 1 placebo capsule with food; and C) placebo, 1 placebo capsule with food and 1 placebo capsule without food. Subjects were asked to take two capsules per day (one active and one placebo based on treatment assignment or two placebo). One capsule was taken with the subjects' evening meal and a second capsule was taken three hours post-meal. The first dosing occurred on the first evening after visit 4. A lipid profile was measured at every visit, and other measurements were taken regularly throughout the study.

Results: One hundred forty-six (146) subjects received at least one dose of study product and had at least one post-randomization lipid measurement. Ninety-six (96) subjects were in the treatment group (i.e., treated with fenofibrate), while fifty (50) subjects were in the placebo. Among the treatment group, fifty-four (54) subjects were administered fenofibrate with food and fort-two (42) were administered fenofibrate without food. One hundred twenty-two (122) subjects completed the study per protocol requirements. Treatment duration was eight weeks.

Efficacy: Among subjects in the treatment group, i.e., during the eight-week treatment with fenofibrate, the prevalence of metabolic syndrome decreased. For example, the number of subjects having three or more criteria (abdominal obesity, HDL cholesterol of less than 40 mg/dl for men and less than 50 mg/dl for women, blood pressure of at least 130/85 mm Hg, fasting glucose of at least 110 mg/dl, and triglycerides of at least 150 mg/dl) decreased by more than 25% in the treatment group (96.9% prevalence reduced to 70.8% prevalence) versus 12% in the placebo (98.0% prevalence reduced to 86.0% prevalence) (chi-square p-value=0.0416). In addition, the prevalence of metabolic syndrome was lower at the end of treatment among the subjects in the fenofibrate with food treatment group (from 96.3% prevalence reduced to 74.1% prevalence) and fenofibrate without food treatment group (from 97.6% prevalence reduced to 66.7% prevalence) as compared to placebo (98.0% prevalence reduced to 86.0% prevalence).

Conclusion: The prevalence of metabolic syndrome among subjects in the treatment groups decreased compared to prevalence of metabolic syndrome in the placebo. The fenofibrate formulation (130 mg) is both safe and efficacious and does not exhibit a food effect and can therefore be taken both with food and without food.

Having thus described presently preferred embodiments of the present invention, it will be appreciated that the objects of the invention have been achieved, and it will be understood by those skilled in the art that changes in construction and widely differing embodiments and applications of the invention will suggest themselves without departing from the spirit and scope of the present invention. The disclosure and description herein are intended to be illustrative and are not in any sense limiting of the invention.

What is claimed is:

1. A method for treating metabolic syndrome in a human, the method comprising: administering a therapeutically effective amount of fenofibrate to a human having metabolic syndrome, wherein a human has metabolic syndrome if the human has at least three characteristics selected from the group consisting of:
   (a) a waist circumference greater than 102 cm for men and greater than 88 cm for women;
   (b) a triglyceride level greater than 150 mg/dl;
   (c) an HDL-cholesterol level less than 40 mg/dl for men and less than 50 mg/dl for women;
   (d) a blood pressure greater than or equal to 130/85 mmHG; and
   (e) a fasting glucose level greater than 110 mg/dl,
   such that after said administering of fenofibrate the human no longer has at least three characteristics selected from the group consisting of (a), (b), (c), (d), and (e).

2. The method of claim 1, wherein the fenofibrate is administered once daily.

3. The method of claim 1, wherein the fenofibrate is administered orally.

4. The method of claim 1, wherein the fenofibrate is in the form of microgranules.

5. The method of claim 4, wherein the microgranules of fenofibrate are administered in a tablet or capsule composition.

6. The method of claim 5, wherein the tablet or capsule composition is an immediate-release formulation.

7. The method of claim 5, wherein the tablet or capsule composition comprises one or more excipients, and wherein the one or more excipients are one or more members selected from the group consisting of a wetting agent, a surfactant, a hydrosoluble carrier, and a binder.

8. The method of claim 4, wherein the microgranules comprise a neutral core, an active layer, and an outer layer encompassing the active layer and neutral core.

9. The method of claim 1, wherein the therapeutically effective amount of fenofibrate is from about 20 to about 400 mg per day.

10. The method of claim 9, wherein the therapeutically effective amount of fenofibrate is from about 30 to about 300 mg per day.

11. The method of claim 10, wherein the therapeutically effective amount of fenofibrate is from about 40 to about 200 mg per day.

12. The method of claim 1, wherein the fenofibrate is administered once daily for a treatment period of at least two weeks.

13. The method of claim 12, wherein the fenofibrate is administered once daily for a treatment period of at least four weeks.

14. The method of claim 13, wherein the fenofibrate is administered once daily for a treatment period of at least eight weeks.

15. A method of lowering triglycerides and increasing HDL-cholesterol in a human, the method comprising administering a therapeutically effective amount of fenofibrate to said human, wherein said human has a triglyceride level greater than 150 mg/dl and an HDL-cholesterol level less than 40 mg/dl for men and less than 50 mg/dl for women, and wherein said human has at least one characteristic selected from the group consisting of:
   (a) a waist circumference greater than 102 cm for men and greater than 88 cm for women;
   (b) a blood pressure greater than or equal to 130/85 mmHG; and
   (c) a fasting glucose level greater than 110 mg/dl,
   such that after said administering of fenofibrate the human has a triglyceride level less than 150 mg/dl and an HDL-cholesterol level greater than 40 mg/dl for men and greater than 50 mg/dl for women and no longer has at least one characteristic selected from the group consisting of (a), (b), and (c).

16. The method of claim 15, wherein the fenofibrate is administered once daily.

17. The method of claim 15, wherein the fenofibrate is administered orally.

18. The method of claim 15, wherein the fenofibrate is in the form of microgranules.

19. The method of claim 18, wherein the microgranules of fenofibrate are administered in a tablet or capsule composition.

20. The method of claim 19, wherein the tablet or capsule composition is an immediate-release formulation.

21. The method of claim 19, wherein the tablet or capsule composition comprises one or more excipients, and wherein the one or more excipients are one or more members selected from the group consisting of a wetting agent, a surfactant, a hydrosoluble carrier, and a binder.

22. The method of claim 18, wherein the microgranules comprise a neutral core, an active layer, and an outer layer encompassing the active layer and neutral core.

23. The method of claim 15, wherein the therapeutically effective amount of fenofibrate is from about 20 to about 400 mg per day.

24. The method of claim 15, wherein the therapeutically effective amount of fenofibrate is from about 30 to about 300 mg per day.

25. The method of claim 15, wherein the therapeutically effective amount of fenofibrate is from about 40 to about 200 mg per day.

26. The method of claim 15, wherein the fenofibrate is administered once daily for a treatment period of at least two weeks.

27. The method of claim 15, wherein the fenofibrate is administered once daily for a treatment period of at least four weeks.

28. The method of claim 15, wherein the fenofibrate is administered once daily for a treatment period of at least eight weeks.

29. The method of claim 1, wherein the human has:
(a) a waist circumference greater than 102 cm for men and greater than 88 cm for women;
(b) a triglyceride level greater than 150 mg/dl; and
(c) an HDL-cholesterol level less than 40 mg/dl for men and less than 50 mg/dl for women prior to the administration of fenofibrate.

30. The method of claim 1, wherein the human has:
(b) a triglyceride level greater than 150 mg/dl;
(c) an HDL-cholesterol level less than 40 mg/dl for men and less than 50 mg/dl for women; and
(d) a blood pressure greater than or equal to 130/85 mmHG prior to the administration of fenofibrate.

31. The method of claim 1, wherein the human has:
(b) a triglyceride level greater than 150 mg/dl;
(c) an HDL-cholesterol level less than 40 mg/dl for men and less than 50 mg/dl for women; and
(e) a fasting glucose level greater than 110 mg/dl
prior to the administration of fenofibrate.

32. The method of claim 29, wherein the human also has a blood pressure greater than or equal to 130/85 mmHG prior to the administration of fenofibrate.

33. The method of claim 29, wherein the human also has a fasting glucose level greater than 110 mg/dl prior to the administration of fenofibrate.

34. A method for treating metabolic syndrome in a human, the method comprising: administering a therapeutically effective amount of fenofibrate to a human having metabolic syndrome, wherein a human has metabolic syndrome if the human has at least three characteristics selected from the group consisting of:
(a) a waist circumference greater than 102 cm for men and greater than 88 cm for women;
(b) a triglyceride level greater than 150 mg/dl;
(c) an HDL-cholesterol level less than 40 mg/dl for men and less than 50 mg/dl for women;
(d) a blood pressure greater than or equal to 130/85 mmHG; and
(e) a fasting glucose level greater than 110 mg/dl;
wherein the fenofibrate is administered as a composition comprising fenofibrate and wherein the composition contains a single surfactant.

35. A method for treating metabolic syndrome in a human, the method comprising: administering a therapeutically effective amount of fenofibrate to a human having metabolic syndrome, wherein a human has metabolic syndrome if the human has at least three characteristics selected from the group consisting of:
(a) a waist circumference greater than 102 cm for men and greater than 88 cm for women;
(b) a triglyceride level greater than 150 mg/dl;
(c) an HDL-cholesterol level less than 40 mg/dl for men and less than 50 mg/dl for women;
(d) a blood pressure greater than or equal to 130/85 mmHG; and
(e) a fasting glucose level greater than 110 mg/dl;
wherein the fenofibrate is administered as a composition comprising granules comprising a neutral core, a layer of fenofibrate surrounding the neutral core, and a layer of hydrosoluble binder surrounding the layer of fenofibrate, wherein the composition contains a single surfactant.

36. The method of claim 34, wherein the surfactant is sodium lauryl sulfate.

37. The method of claim 36, wherein the fenofibrate and sodium lauryl sulfate are present co-micronized.

38. The method of claim 34, wherein after said administering of fenofibrate the human no longer has at least three characteristics selected from the group consisting of (a), (b), (c), (d), and (e).

39. The method of claim 35, wherein the surfactant is sodium lauryl sulfate.

40. The method of claim 35, wherein after said administering of fenofibrate the human no longer has at least three characteristics selected from the group consisting of (a), (b), (c), (d), and (e).

* * * * *